(12) United States Patent
Lee et al.

(10) Patent No.: US 6,388,083 B2
(45) Date of Patent: May 14, 2002

(54) PROCESS FOR THE SYNTHESIS OF (2S)-PHENYL-3-PIPERIDONE

(75) Inventors: Jaemoon Lee, Edison; David Askin, Warren; Thoa Hoang, Iselin, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/899,633

(22) Filed: Jul. 5, 2001

Related U.S. Application Data

(60) Provisional application No. 60/216,894, filed on Jul. 7, 2000.

(51) Int. Cl.$^7$ ................... C07D 211/02; C07D 211/42
(52) U.S. Cl. ...................................... 546/216
(58) Field of Search .......................................... 546/216

(56) References Cited

PUBLICATIONS

Lee et al., "Asymmetric synthesis of (2R, 3S)–3–hydroxy–2–phenylpiperidine via ring expansion", Tet. Lett. (2001), 42(36), 6223–6225.*

* cited by examiner

*Primary Examiner*—Patricia L. Morris
(74) *Attorney, Agent, or Firm*—J. Eric Thies; Melvin Winokur

(57) ABSTRACT

The present invention is concerned with novel processes for the preparation of (2S)-phenyl-3-piperidone. This compound is useful as an intermediate in the synthesis of compounds which possess pharmacological activity.

14 Claims, No Drawings

PROCESS FOR THE SYNTHESIS OF (2S)-PHENYL-3-PIPERIDONE

This application claims benefit of 60/216,894 filed Jul. 7, 2000.

BACKGROUND OF THE INVENTION

The present invention relates to processes for the preparation of (2S)-phenyl-3-piperidone which is useful as an intermediate in the preparation of certain therapeutic agents. In particular, the present invention provides a process for the preparation of (2S)-phenyl-3-piperidone which is an intermediate in the synthesis of pharmaceutical compounds which are substance P (neurokinin-1) receptor antagonists.

The general processes disclosed in the art for the preparation of compounds related to (2S)-phenyl-3-piperidone employ a relatively high number of steps and require a resolution of the desired product (Calvez, et al., *Tetrahedron Letters*, 40, 7099–7100 (1999); Tomooka, et al., *J. Am. Chem. Soc.*, 122, 408–409 (2000); Wallace, et al., *Tetrahedron Letters*, 41, 2027–2029 (2000); EPO Patent Publication 0 528 495; PCT Patent Publication WO 97/49710). In contrast to the previously known processes, the present invention provides effective methodology for the preparation of (2S)-phenyl-3-piperidone in relatively low number of steps and without requiring resolution.

It will be appreciated that (2S)-phenyl-3-piperidone is an important intermediate for a particularly useful class of therapeutic agents. As such, there is a need for the development of a process for the preparation of (2S)-phenyl-3-piperidone which is readily amenable to scale-up, uses cost-effective and readily available reagents and which is therefore capable of practical application to large scale manufacture.

Accordingly, the subject invention provides a process for the preparation of (2S)-phenyl-3-piperidone via a very simple, short, relatively inexpensive and highly efficient synthesis.

SUMMARY OF THE INVENTION

The novel process of this invention involves the synthesis of (2S)-phenyl-3-piperidone. In particular, the present invention is concerned with novel processes for the preparation of a compound of the formula:

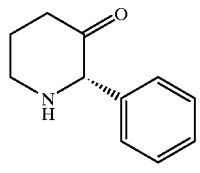

This compound is an intermediate in the synthesis of compounds which possess pharmacological activity. In particular, such compounds are substance P (neurokinin-1) receptor antagonists which are useful e.g., in the treatment of psychiatric disorders, inflammatory diseases, and emesis.

DETAILED DESCRIPTION OF THE INVENTION

The present invention is directed to processes for the preparation of (2S)-phenyl-3-piperidone of the formula:

The general process for the preparation of (2S)-phenyl-3-piperidone may be depicted as follows:

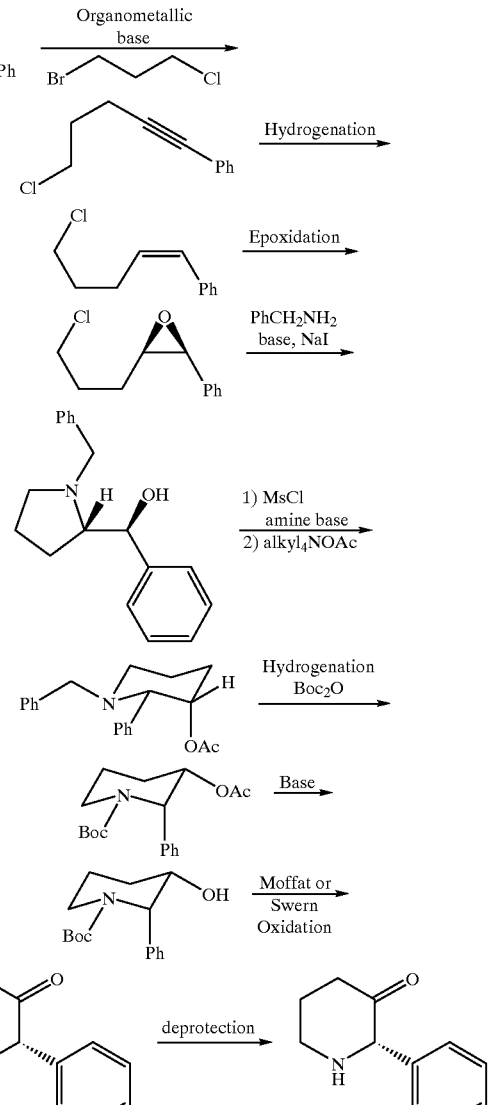

In accordance with the present invention, the subject process provides (2S)-phenyl-3-piperidone in higher yields and in a more efficient route than the processes disclosed in the art.

In a preferred embodiment, the present invention is directed to a process for the preparation of (2S)-phenyl-3-piperidone which may be depicted as follows:

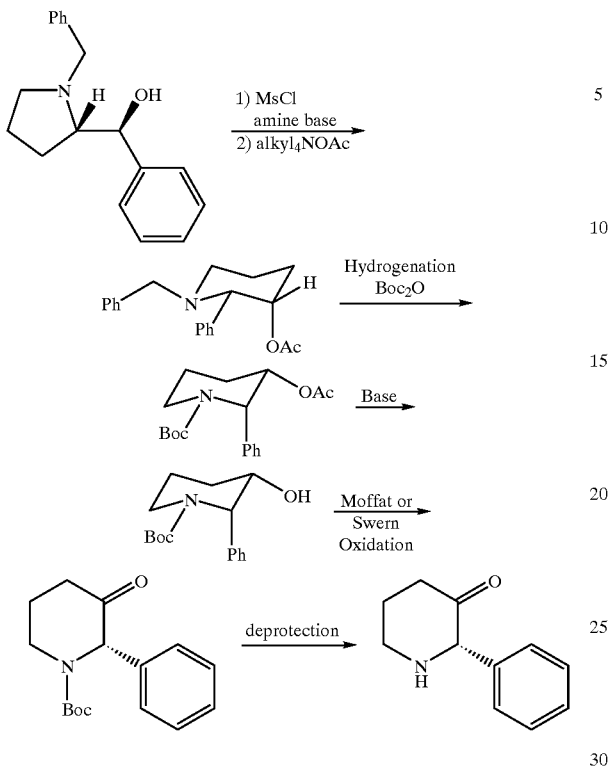

A specific embodiment of the present invention concerns a process for the preparation of (2S)-phenyl-3-piperidone of the formula:

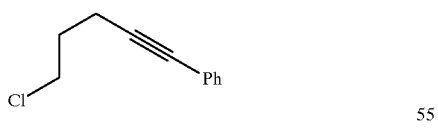

which comprises:

reacting phenylacetylene with an organometallic base followed by 1-bromo-3-chloropropane to give a compound of the formula:

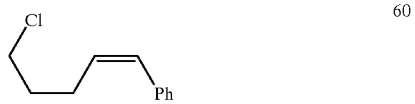

which compound is reduced under hydrogenation conditions to give a compound of the formula:

which compound is oxidized to give a compound of the formula:

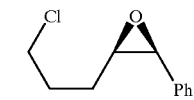

which compound is reacted with benzyl amine to give a compound of the formula:

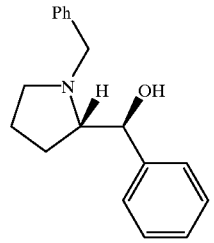

which compound is reacted with methanesulfonyl chloride in the presence of an amine base followed by reaction with a tetra-alkylammonium acetate to give a compound of the formula:

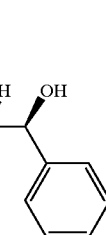

which compound is deprotected under hydrogenation conditions followed by reaction with tert-butyloxycarbonyl anhydride to give a compound of the formula:

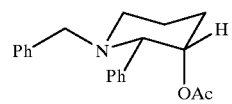

which compound is hydrolysed with a base to give a compound of the formula:

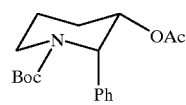

which compound is oxidized under Moffat or Swern conditions to give a compound of the formula:

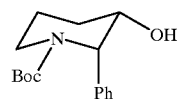

which compound is deprotected to give (2S)-phenyl-3-piperidone of the formula:

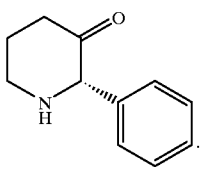

In the reaction of phenylacetylene with an organometallic base followed by 1-bromo-3-chloropropane to give a compound of the formula:

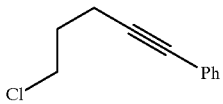

it is preferred that the reaction is conducted: in an aprotic solvents such as tetrahydrofuran, diethyl ether or dimethoxyethane; the organometallic base is and alkyl or aryl lithium reagents, such as n-butlyl, methyl, hexyl or phenyl lithium or with a Grignard reagents, such as i-propyl MgCl, Bu-MgCl, PhenylMgBr (or Cl). Alternatively, sodium amide in DMSO may be employed for deprotonation of phenyl acetylene.

In the reduction under hydrogenation conditions of the compound of the formula:

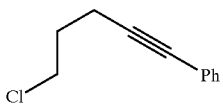

to give a compound of the formula:

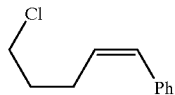

it is preferred that the hydrogenation is catalytic hydrogenation, such as with a Lindlar catalyst. It is futher preferred that a catalytic poison, such as quinoline, thiophene, sulfur, lutidine or collidine is present. Appropriate solvents include ethyl acetate, MeOH, EtOH, i-propanol and IPAC.

In the oxidation of the compound of the formula:

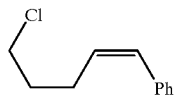

to give a compound of the formula:

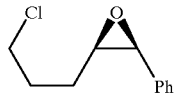

it is preferred that the oxidation is conducted under Jacobsen epoxidation conditions. Preferred oxidation agents include peracids such as N-phenylpyridine-N-oxide, mCPBA or peracetic acid. Use of the catalyst (R,R)-(−)-N,N'-bis(3,5- di-tert-butylsalicylidene)- 1.2-cyclo-hexanediarninomanganese(iii)chloride is also preferred. Preferred temperatures are below 0° C. or between 0° C. and −60° C.

In the reaction of the compound of the formula:

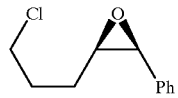

with benzyl amine to give a compound of the formula:

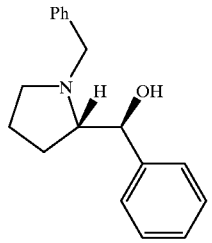

it is preferred that the solvent is acetonitrile, propionitrile or nitromethane. Sodium iodide is optionally present.

In the reaction of the compound of the formula:

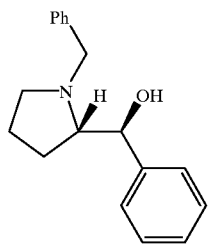

with methanesulfonyl chloride in the presence of an amine base followed by reaction with a tetra-alkylammonium acetate to give a compound of the formula:

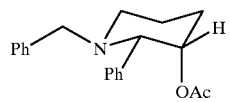

it is preferred that methanesulfonyl chloride is employed, although the N-benzyl hydroxy-pyrolidine may be converted to aziridinum halides, ie; bromide with sulfonic halides such as toluenesulfonic chloride/ bromide, bromobenzene sulfonic chloride, p-nitrobenzenesulfonic chloride in various aprotic solvents including DME, diethyl ether, methylene chloride, dichloroethane or acetonitrile. It is preferred that the tetra-alkylammonium acetate is tetrabutyl ammonium acetate or a benzoate or carboxylic acid ($C_1$–$C_{20}$) ammonium salt including alkaline metal salt, such as Li, Na, K. The temperature of the reaction mixture is preferably below −20° C.

In the deprotection of the compound of the formula:

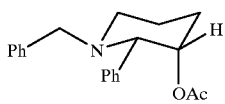

followed by reaction with tert-butyloxycarbonyl anhydride to give a compound of the formula:

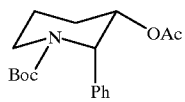

it is preferred that the deprotection is conducted under catalytic hydrogenation conditions.

In the hydrolysis of the compound of the formula:

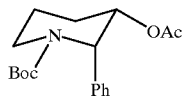

with a base to give a compound of the formula:

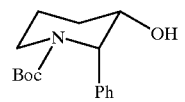

it is preferred that the hydrolysis is conducted with aqueous alkaline hydroxide, such as with NaOH, LiOH, KOH, or $K_2CO_3$, $Na_2CO_3$ in MeOH, EtOH or THF.

In the oxidation of the compound of the formula:

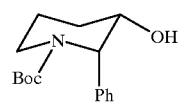

under Moffat or Swern conditions to give a compound of the formula:

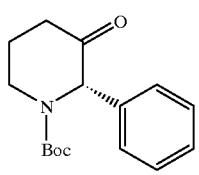

it is preferred that Moffat conditions with dimethyl sulfoxide, 1-(3-dimethylaminopropyl)-3-ethylcarbodiimide and pyridine are employed.

In a preferred embodiment, the present invention is directed to a process for the preparation of (2S)-phenyl-3-piperidone of the formula:

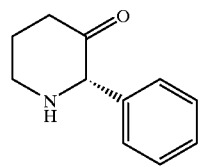

which comprises:
  reacting a compound of the formula:

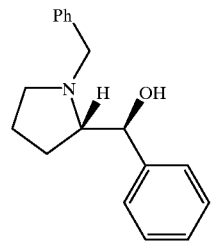

with methanesulfonyl chloride in the presence of an amine base followed by reaction with a tetra-alkylammonium acetate to give a compound of the formula:

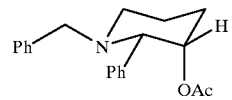

which compound is deprotected under hydrogenation conditions followed by reaction with tert-butyloxycarbonyl anhydride to give a compound of the formula:

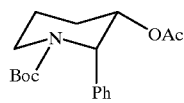

which compound is hydrolysed with a base to give a compound of the formula:

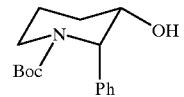

which compound is oxidized under Moffat or Swern conditions to give a compound of the formula:

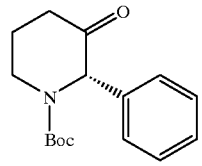

which compound is deprotected to give (2S)-phenyl-3-piperidone of the formula:

9

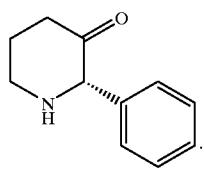

An alternate embodiment of the present invention concerns a process for the preparation of (2S)-phenyl-3-piperidone of the formula:

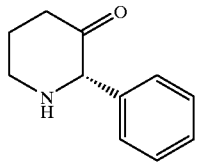

which comprises the process:

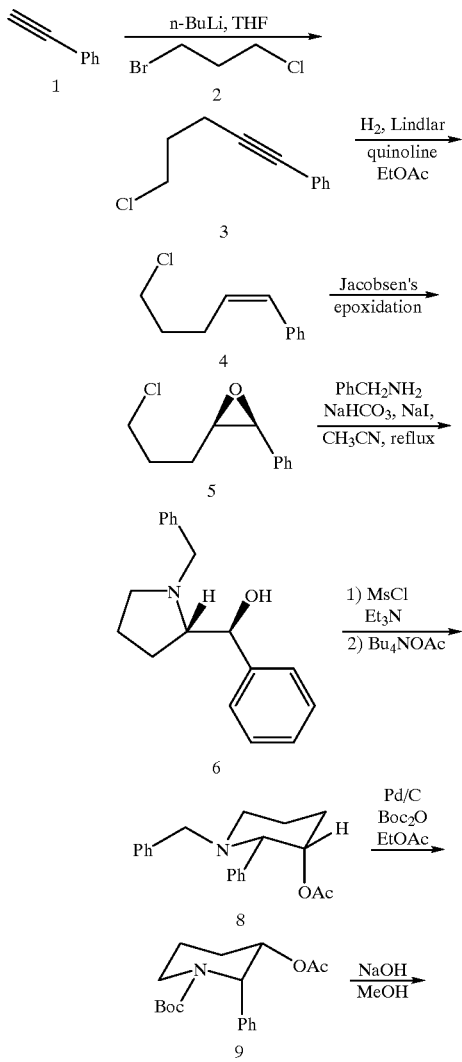

10

-continued

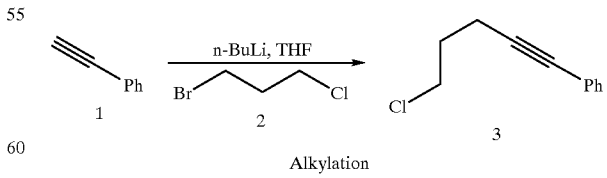

This alternate embodiment of the subject process involves Jacobsen's asymmetric epoxidation of the cis-olefin 4 to give the cis-epoxide 5. Treatment of the chloro cis-epoxide with benzyl amine in acetonitrile at reflux affords the five-membered hydroxy pyrolidine 6. Ring expansion of five-membered N-benzylpyrolidine-alcohol 6 to piperidine 8 is realized via following sequences. First, the hydroxypyrrolidine 6 is treated with methanesulfonyl chloride at —20° C. in which no chloro piperidine formed. Subsequent treatment of the aziridinum chloride 7 with tetrabutylammonium acetate (–20° C. to room temperature) affords the desired acetoxypiperidine 8. Selective hydrogenation of N-benzyl piperidine using Pd/C in the presence of Boc$_2$O gives the desired Boc-protected piperidine acetate 9. Then, the resulting acetate was hydrolyzed to N-Boc-(2S, 3S)-3-hydroxy-2-phenylpiperidine 10 using NaOH in MeOH (95%). Well-established epimerization free oxidation of the resulting Boc-piperidinol under Moffat or Swern condition gives the N-Boc-(2S)-phenyl-3-piperidinone which is deprotected to provide (2S)-phenyl-3-piperidinone 11.

The (2S)-phenyl-3-piperidone obtained in accordance with the present invention may be used as starting material in further reactions directly or following purification. Similarly, the N-Boc-(2S)-phenyl-3-piperidinone may be used as starting material in further reactions without deprotection to (2S)-phenyl-3-piperidinone.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

Alkylation

In a 2 L round bottom flask was placed phenylacetylene 1 (60 g, 587 mmol) in THF (600 mL). nBuLi was added dropwise at −78° C. for 20 mins. The reaction mixture was warmed up slowly to ambient temperature where 1-bromo-3-chloropropane (258 mL, 646 mmol) was added and the solution was heated to reflux for 31 hours. The crude mixture then was evaporated and diluted with EtOAc 25 (300 mL), washed with 200 ml water, 100 ml brine, filtered over silica gel and concentrated to give 104 g product as a brown oil.

$^1$H NMR: 2.07(q, 2H), 2.62(t, 2H), 3.72(t, 2H), 7.29 (m, 3H), 7.40(m, 2H).

EXAMPLE 2

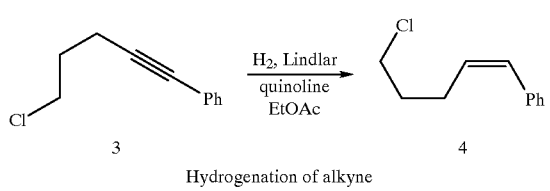

Hydrogenation of alkyne

The hydrogenation was conducted under 15 psi, at 23° C. where 50 g of starting material was used, with 2.6 g quinoline, 5 g Pd/C Lindlar in 500 mL EtOAc. The crude mixture was filtered through celite and silica gel, then evaporated to 250 mL, washed with 100 mL 0.5N HCl, evaporated to dryness to give 50.5 g product as a brown oil (84% yield for the first 2 steps). $^1$H NMR: 1.94 (q, 2H), 2.50 (t, 2H), 3.55(t, 2H), 5.64 (m, 1H), 6.5 (d, 1H), 7.23 (m, 3H), 7.47 (m, 2H).

EXAMPLE 3

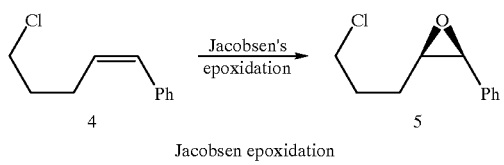

Jacobsen epoxidation

In a 500 mL flask was placed the cis-olefin 4 (48 g, 84% purity, 223 mmol) in methylene chloride (240 ml), N-phenylpyridine-N-oxide (PPO) (6.83 g, 40 mmol), (R,R)-(−)-N,N'-Bis(3,5-di-tert-butylsalicylidene)- 1,2-cyclohexanediaminomanganese(iii)chloride (8.44 g, 13.2 mmol), NaCl (30 g) were added and the reaction was cooled to 0° C., then NaOCl (168 ml, 13%) was added dropwise for 10 min. Then the reaction was aged at 5° C. for 2 days. The crude was washed with 1 L sat. NH$_4$Cl, back extracted with 3×500 mL EtOAc, then washed again with 300 mL brine, dried over Na$_2$SO$_4$ and evaporated. The residue was chromatographed on a silica gel column (hexanes, then 1%, 2%, 3% EtOAc in hexanes was used) to give 27.4 g epoxide (62% yield, 92% ee). $^1$H NMR: 1.49 (q, 2H), 1.92 (m, 2H), 3.25 (m, 1H), 3.48 (t, 2H), 4.11 (d, 1H), 7.32 (m, 5H). $^{13}$C NMR: 24.4, 29.3, 44.4, 57.4, 58.6, 126.4, 127.7, 128.2, 135.3.

EXAMPLE 4

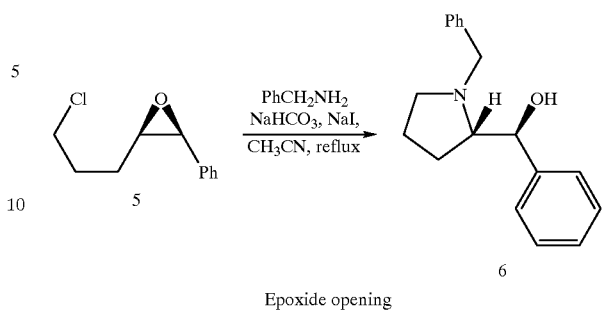

Epoxide opening

A mixture of cis-epoxide 5 (17 g, 86.5 mmol), benzylamine (9.9 ml, 90.8 mmol), and 7.4 g NaHCO$_3$ was refluxed in 200 ml of acetonitrile for 25 hours to give N-benzyl hydroxy-pyroridine 6 in 58% conversion. The crude mixture was diluted with 100 ml of EtOAc, washed with 200 mL NaHCO$_3$, and back extracted with 2×100 mL of EtOAc. Then, the combined organic layers were concentrated under rotarap. The brown crude oil was flash chromatographed on the silica gel (9:1 then 8: 2 hex: EtOAc) to give 12 g of N-benzyl hydroxy-pyroridine 6 as a yellow solid (47% yield).

$^1$H NMR: 1.79 (m, 3H), 1.96 (m, 1H), 2.43 (m, 1H), 2.98(m, 1H), 3.10 (m, 1H), 3.37 (d, 1H), 3.68 (d, 1H), 4.41 (d 1H), 7.37 (m, 10H).

EXAMPLE 5

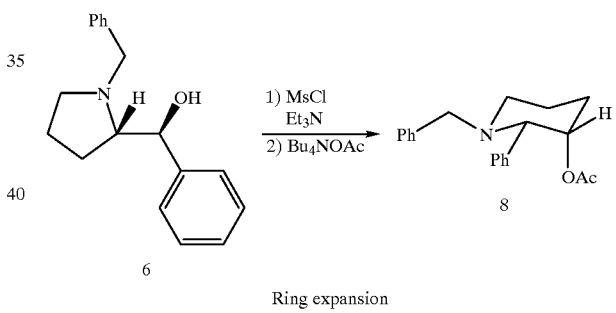

Ring expansion

N-benzyl hydroxy-pyrolidine 6 (6.65 g, 22.4 mmol) was placed in THF (110 ml) and cooled to −20° C. where methane sulfonic chloride (2.08 ml, 26.87 mmol) was introduced into the solution followed by triethylamine (12.5 ml, 89.6 mmol). Then, the resulting solution was aged for 1 hour at this temperature. Tetra-butyl ammonium acetate (39 g, 129 mmol) was added and the resulting mixture was wormed to room temperature over a period of 1 h. After aging for 16 h at room temperature, the reaction mixture was extracted with 2×200 mL of EtOAc and washed sequentially with 100 ml of sat. NaHCO$_3$, and 50 ml brine. After concentration, the crude mixture was purified by flash chromatographed on silica gel (9:1, 8:2, 7:3 hex: EtOAc) followed by recrystallization from EtOAC-hexanes to afford the desired acetoxypiperidine 8 in 85 % yield (mp 105° C., 99% ee).

$^1$H NMR: 1.55 (m, 1H), 1.56(m, 1H), 1.93(s, 3H), 2.06(m, 3H), 2.95(d, 1H), 3.05(d, 1H), 3.41(d, 1H), 3.84(d, 1H), 5.03(d, 1H), 7.28(m, 8H), 7.47(d, 2H); $^{13}$C NMR: 20.5, 21.1, 29.4, 52.8, 59.7, 70.3, 71.7, 126.8, 127.4, 128.1, 128.1, 128.7, 128.9, 170.2.

EXAMPLE 6

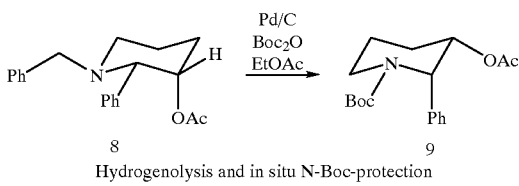

Hydrogenolysis and in situ N-Boc-protection

To a stirred solution of the Acetoxypiperidine 8 (3.63 g, 11 mmol) in 70 ml EtOAc was added 0.98 g of 10 % Pd/C and 2.54 g of Boc$_2$O (11.6 mmol). The resulting solution was agitated under hydrogen atmosphere (40 psi ) for 24 h. The crude mixture was filtered over the pad of Celite and evaporated to give 3.3 g of N-Boc-piperidine 9 as a yellow oil (87% yield).

$^1$H NMR: 1.43(s, 9H), 1.55(m, 2H), 1.75(m, 2H), 1.92(m, 2H), 2.00(s, 3H), 2.86(m, 1H), 4.01(d, 1H), 5.15(q, 1H), 5.53(d, 1H), 7.31(m, 3H), 7.42(d, 2H).

EXAMPLE 7

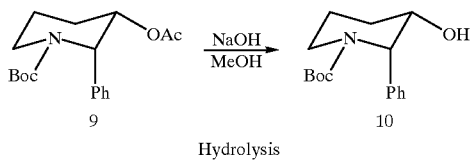

Hydrolysis

To a stirred solution of 3.2 g (9.16 mmol) of N-Boc-piperidine 9 in 50 mL of MeOH was treated with 16 ml of 5 N NaOH at 23° C. After stirred at this temperature for 16 h, solvent was removed using rotarap and extracted with 30 mL EtOAc. Then, organic layer was concentrated to give 2.7 g product (95 % yield).

$^1$H NMR: 1.35(s, 9H), 1.69(m, 1H), 1.82(m, 3H), 3.04(t, 1H), 4.00(dd, 1H), 4.09(m, 1H), 5.33(d, 1H), 7.29(m, 1H), 7.33(m, 2H), 7.47(d, 2H).

EXAMPLE 8

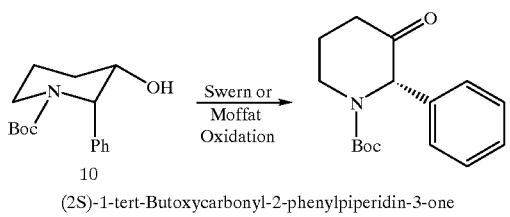

(2S)-1-tert-Butoxycarbonyl-2-phenylpiperidin-3-one

Dimethyl sulfoxide (20.80 mL, 22.90 g, 29.3 mmol) in dichloro-methane (75 mL) was added dropwise to a cooled (−70° C.) solution of oxalyl chloride (13.96 mL, 20.30 g, 160 mmol) in dichloromethane (350 mL). The mixture was stirred at −70° C. for 15 min., then (2S,3S)-1-tert-butoxycarbonyl-3-hydroxy-2-phenylpiperidine (36.91 g. 133 mmol) in dichloromethane (150 mL) was added dropwise. The mixture was stirred at −70° C. for 20 min., then allowed to warm to −30° C. The mixture was cooled to —50° C. and triethylamine (55.95 mL, 40.45 g, 400 mmol) was added slowly. The mixture was allowed to warm to 0° C. and diluted with ice-cooled dichloromethane (250 mL). The mixture was washed with ice cold aqueous citric acid solution (5%, 2×300 mL) and water (300 mL), dried (MgSO4), and the solvent was evaporated under reduced pressure to give (2S)-1-tert-butoxycarbonyl-2-phenylpiperidin-3-one as a yellow oil (42.3 g). $^1$H NMR (250 MHz, CDC13) 7.5–7.3(5H, m), 5.8 (1H, br s), 4.2(1H, br s), 3.4 (1H, m), 2.6 (2H, m), 2.0 (2H, 1.54 (9H, s).

Alternatively, dimethyl sulfoxide (20.80 mL, 22.90 g, 29.3 mmol) in dichloromethane (75 mL) is added dropwise to a cooled (0° C.) solution of 1-(3-dimethylaminopropyl)-3-ethylcarbodiimide (160 mmol) in dichloromethane (350 mL). The mixture is stirred at 0° C. for 15 min., then (2S,3S)-1-tert-butoxycarbonyl-3-hydroxy-2-phenylpiperidine (36.91 g. 133 mmol) in dichloromethane (150 mL) is added dropwise. The mixture was stirred at 0° C. for 20 min and pyridine (400 mmol) is added slowly followed by trifluroacetic acid (400 mmol). The mixture is allowed to warm to 0° C. and diluted with ice-cooled dichloromethane (250 mL). The mixture is washed with ice cold aqueous citric acid solution (5%, 2×300 mL) and water (300 mL), dried (MgSO4), and the solvent is evaporated under reduced pressure to give (2S)-1-tert-butoxycarbonyl-2-phenylpiperidi n-3-one.

EXAMPLE 9

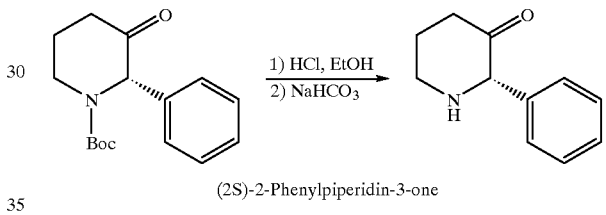

(2S)-2-Phenylpiperidin-3-one

Trifluoroacetic acid (4 mL) is added to a stirred, cooled (0° C.) solution of (2S)- 1-tert-butoxycarbonyl-2-phenylpiperidin-3-one (40 mg) in methylene chloride (2 mL) and the mixture is stirred at room temperature for 3 h. The solvent is evaporated under reduced pressure and the residue is partitioned between aqueous saturated sodium bicarbonate (50 ml) and ethyl acetate (3×50 ml). The combined organic fractions are washed with brine (50 ml), dried (MgSO4) and evaporated in vacuo to give (2S)-2-phenylpiperidin-3-one.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

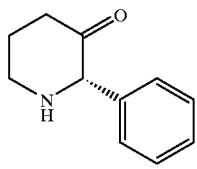

which comprises:

reacting phenylacetylene with an organometallic base followed by 1-bromo-3-chloropropane to give a compound of the formula:

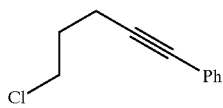

which compound is reduced under hydrogenation conditions to give a compound of the formula:

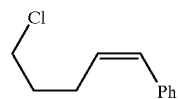

which compound is oxidized to give a compound of the formula:

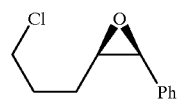

which compound is reacted with benzyl amine to give a compound of the formula:

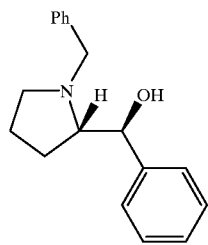

which compound is reacted with methanesulfonyl chloride in the presence of an amine base followed by reaction with a tetra-alkylammonium acetate to give a compound of the formula:

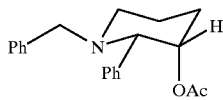

which compound is deprotected under hydrogenation conditions followed by reaction with tert-butyloxycarbonyl anhydride to give a compound of the formula:

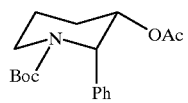

which compound is hydrolysed with a base to give a compound of the formula:

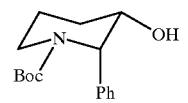

which compound is oxidized under Moffat or Swern conditions to give a compound of the formula:

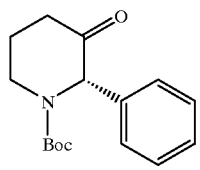

which compound is deprotected to give (2S)-phenyl-3-piperidone of the formula:

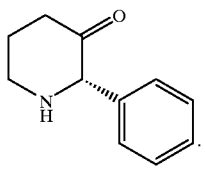

2. The process of claim 1 wherein the reaction of phenylacetylene with an organometallic base followed by 1-bromo-3-chloropropane to give a compound of the formula:

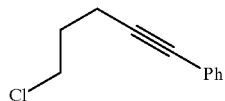

the organometallic base is an alkyl or aryl lithium reagent selected from the group consisting of: n-butlyl, methyl, hexyl and phenyl lithium; or is a Grignard reagent selected from the group consisting of i-propyl-MgCl, butyl-MgCl, phenyl-MgBr, and phenyl-MgBCl.

3. The process of claim 1 wherein the reduction under hydrogenation conditions of the compound of the formula:

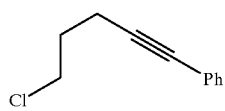

to give a compound of the formula:

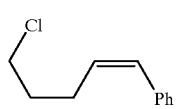

the hydrogenation is catalytic hydrogenation.

4. The process of claim 3 wherein the catalytic hydrogenation is conducted with a Lindlar catalyst.

5. The process of claim 3 wherein the catalytic hydrogenation is conducted in the presence of a catalytic poison selected from the group consisting of:
quinoline, thiophene, sulfur, lutidine and collidine.

6. The process of claim 1 wherein the oxidation of the compound of the formula:

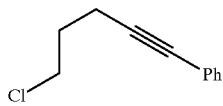

to give a compound of the formula:

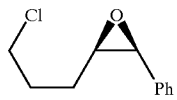

the oxidation is conducted under Jacobsen epoxidation conditions.

7. The process of claim 6 wherein the oxidation is conducted with a peracid selected from the group consisting of N-phenylpyridine-N-oxide, mCPBA and peracetic acid.

8. The process of claim 6 wherein the oxidation is conducted in the presence of (R,R)-(−)—N,N'-bis(3,5-di-tert-butylsalicylidene)- 1,2-cyclo-hexanediaminomanganese (iii)chloride as a catalyst.

9. The process of claim 1 wherein the reaction of the compound of the formula:

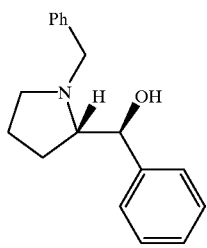

with methanesulfonyl chloride in the presence of an amine base followed by reaction with a tetra-alkylammonium acetate to give a compound of the formula:

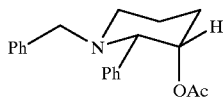

the tetra-alkylammonium acetate is tetra-butyl ammonium acetate or a benzoate or carboxylic acid (C1–C20) ammonium salt.

10. The process of claim 1 wherein the deprotection of the compound of the formula:

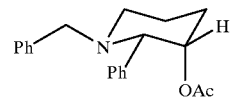

followed by reaction with tert-butyloxycarbonyl anhydride to give a compound of the formula:

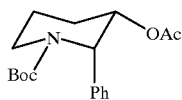

the deprotection is conducted under catalytic hydrogenation conditions.

11. The process of claim 1 wherein the hydrolysis of the compound of the formula:

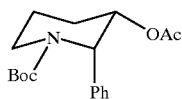

with a base to give a compound of the formula:

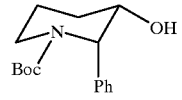

the hydrolysis is conducted with aqueous alkaline hydroxide, selected from the group consisting of NaOH, LiOH, KOH, or $K_2CO_3$, $Na_2CO_3$.

12. The process of claim 11 wherein the hydrolysis is conducted in a solven comprising water, MeOH, EtOH, THF, and mixtures thereof.

13. The process of claim 1 wherein the oxidation of the compound of the formula:

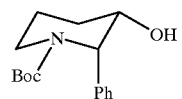

under Moffat or Swern conditions to give a compound of the formula:

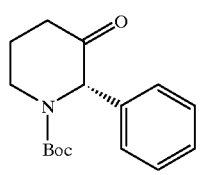

the oxidation is conducted under Moffat conditions with dimethyl sulfoxide, 1-(3-dimethylaminopropyl)-3-ethylcarbodiimide and pyridine.

14. A process for the preparation of (2S)-phenyl-3-piperidone of the formula:

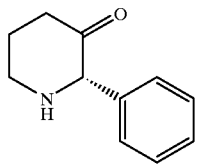

which comprises:

reacting a compound of the formula:

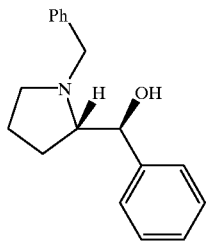

with methanesulfonyl chloride in the presence of an amine base followed by reaction with a tetra-alkylammonium acetate to give a compound of the formula:

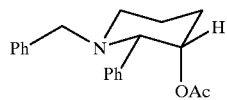

which compound is deprotected under hydrogenation conditions followed by reaction with tert-butyloxycarbonyl anhydride to give a compound of the formula:

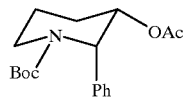

which compound is hydrolysed with a base to give a compound of the formula:

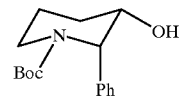

which compound is oxidized under Moffat or Swern conditions to give a compound of the formula:

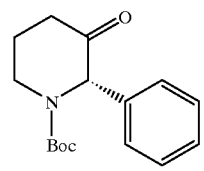

which compound is deprotected to give (2S)-phenyl-3-piperidone of the formula:

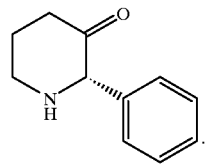

\* \* \* \* \*